United States Patent [19]

Crisp et al.

[11] 4,337,186
[45] Jun. 29, 1982

[54] HARDENABLE COMPOSITIONS

[75] Inventors: Stephen Crisp, Hounslow; Alan D. Wilson, Liphook, both of England

[73] Assignee: National Research Development Corporation, England

[21] Appl. No.: 166,980

[22] PCT Filed: Jan. 17, 1979

[86] PCT No.: PCT/GB79/00014

§ 371 Date: Sep. 17, 1979

§ 102(e) Date: Aug. 9, 1979

[87] PCT Pub. No.: WO79/00521

PCT Pub. Date: Aug. 9, 1979

[30] Foreign Application Priority Data

Jan. 17, 1978 [GB] United Kingdom ............... 01833/78

[51] Int. Cl.$^3$ .......................... C08K 3/22; C08K 3/40; C08K 5/09; A61K 5/06
[52] U.S. Cl. .............................. 525/362; 260/998.11; 524/650; 524/5; 523/116; 525/363; 525/329
[58] Field of Search ...................... 260/29.6 S, 29.6 H, 260/29.6 M, DIG. 36, 42.52, 998.11, 42.13

[56] References Cited

U.S. PATENT DOCUMENTS

| 3,814,717 | 6/1974 | Wilson et al. | 260/42.13 |
|---|---|---|---|
| 3,856,737 | 12/1974 | Foster et al. | 260/29.6 M |
| 3,962,267 | 6/1976 | Suzuki et al. | 260/29.6 H |
| 3,986,998 | 10/1976 | Schmitt et al. | 260/29.6 H |
| 4,016,124 | 4/1977 | Crisp et al. | 260/29.6 H |
| 4,082,722 | 4/1978 | Schmitt et al. | 260/29.6 H |
| 4,089,830 | 5/1978 | Tezuka | 260/29.6 H |
| 4,107,845 | 8/1978 | Lee et al. | 260/42.52 |
| 4,141,144 | 2/1979 | Lustgarten | 260/42.52 |
| 4,154,717 | 5/1979 | Kohmura et al. | 260/42.13 |
| 4,209,434 | 6/1980 | Wilson et al. | 260/29.6 H |

FOREIGN PATENT DOCUMENTS

| 2439882 | 3/1975 | Fed. Rep. of Germany ... 260/29.6 H |
|---|---|---|
| 115598 | 3/1969 | United Kingdom . |
| 1366031 | 9/1974 | United Kingdom . |
| 1407013 | 9/1975 | United Kingdom . |
| 1422337 | 1/1976 | United Kingdom . |
| 1450557 | 9/1976 | United Kingdom . |
| 1463173 | 2/1977 | United Kingdom . |
| 1484454 | 9/1977 | United Kingdom . |
| 1495255 | 12/1977 | United Kingdom . |
| 1504520 | 3/1978 | United Kingdom . |

OTHER PUBLICATIONS

Derwent Abs. 69496/U46, "Dental Cements ... Chelating Agents to Accelerate Setting", Oct. 25, 1973.
Derwent Abst. 20238A/11, "Aqueous Hardening Soln for Dental Cement ... ", Jan. 31, 1978, G. C. Shika Kogyo.
Journal of Dental Research, 55, No. 6, 1408–1413, Sep.–Dec. 1974.

Primary Examiner—John C. Bleutge
Assistant Examiner—Hebert Lilling
Attorney, Agent, or Firm—Jacobs & Jacobs

[57] ABSTRACT

Compositions which are hardenable in the presence of water to form a poly(carboxylate) cement contain a metal salt which accelerates the setting of the composition.

27 Claims, No Drawings

HARDENABLE COMPOSITIONS

This invention relates to hardenable compositions comprising a particulate ion-leachable silicate or aluminosilicate; to cement packs comprising a particulate ion-leachable silicate or aluminosilicate and a poly(carboxylic acid); to hardened cements formed by reacting the particulate ion-leachable silicate or aluminosilicate with the poly(carboxylic acid) in the presence of water; to processes for preparing such cements; to mixtures useful in preparing such cements; and to products formed by utilising the cements.

In our Complete Specification No. 1,422,337 we have disclosed that improvement in the rate of hardening of such cements, conventionally called "poly(carboxylate) cements", is obtained by the addition thereto of a chelating agent. Specifically, we have described and claimed a process for the production of a poly(carboxylate) cement which comprises mixing a water-soluble poly(carboxylic acid) having a relative viscosity from 1.05 to 2.00 with a cement powder in the presence of a water-soluble chelating agent and water to a give a plastic mass which rapidly hardens to form a poly(carboxylate) cement. We have also described and claimed poly(carboxylate) cement packs and cement-forming liquids for the use in such processes, as well as poly(carboxylate) cements formed by such processes.

It is desirable to be able to improve still further the control over setting times for poly(carboxylate) cements, particularly having regard to the diverse and often specialised applications to which these cements are increasingly being put.

According to the present invention, there is provided a hardenable composition which comprises (i) a poly(-carboxylic acid) or precursor thereof (as herein defined); (ii) a particulate ion-leachable silicate or aluminosilicate reactable with (i) in the presence of water or set to a hardened composition; and (iii) a metal salt which accelerates the setting of the composition.

It has been found that certain silver (I) salts or barium salts, for example silver nitrate, barium chloride or barium fluoride, may be utilised in accordance with compositions of this invention. However, in general (iii) comprises a multivalent metal salt the cation of which either has a high ionic potential (ionic charge/ionic radius), generally above 2.1, or is capable of forming complexes. Apart from the above mentioned exceptions, it is found empirically that such cations are those of a metal less electropositive than sodium, generally having a standard electrode potential $E_{ox}^o$ less than 2.6 volts. Suitable such salts are those of aluminum, cadmium, magnesium, mercury (II), silver (II) or zirconium, especially aluminium, magnesium, silver (II) or zirconium. Further suitable such salts are the fluorides, for example aluminium fluoride, magnesium fluoride, stannous fluoride, silver (II) fluoride or zinc fluoride.

Preferably, such salts (iii) are soluble in an aqueous solution of (i).

In accordance with a further aspect of the invention, there is provided a hardenable composition as hereinabove defined which further comprises a complexing agent soluble in an aqueous solution of (i). The complexing agent may comprise a fluoride ligand or, more preferably, a chelating agent. The chelating agent may comprises a plurality of carboxyl groups, for example aconitic, itaconic, maleic mellitic or tricarballic acid; it may also comprise at least one hydroxyl group. Particularly preferred such chelating agents comprise citric, malic or tartaric acid. A further suitale type of chelating agent comprises a multivalent metal chelate, the metal of which may suitably be the same as that in (iii), for example a beta-diketone chelate, such as is formed by aluminium or chromium, or an EDTA chelate, such as is formed by copper or zinc.

Such chelating agents are suitable present in an amount up to 20% by weight, preferably 0.1% to 10% by weight, especially 3% to 8 % by weight, based on the weight of (i).

Preferred hardenable compositions according to this invention are those which comprise a chelating agent as hereinabove described and wherein (III) comprises a multivalent metal fluoride, including barium fluoride; or a multivalent metal chloride, including copper, stannous and zinc chloride, the cation of which has a standard electrode potential $E_{ox}^o$ less than 2.6 volts.

Suitably (iii) is present in an amount of up to 15% by weight, preferably 1% to 10% by weight, based on the weight of (i). Desirably, the weight ratio of (iii) to the chelating agent is from 15:1 to 1:15, preferably 3:1 to 1:3.

The preferred poly(carboxylic acids) suitable for use as (i) are those prepared by the homopolymerisation and copolymerisation of unsaturated aliphatic carboxylic acids for example aconitic acid, acrylic acid, citraconic acid, fumaric acid, glutaconic acid, itaconic acid, maleic acid, mesaconic acid, methacrylic acid, and tiglic acid; and the copolymerisation of these acids with other unsaturated aliphatic monomers for example vinyl monomers, such as vinyl hydrocarbon monomers, vinyl ethers, acrylamide or acrylonitrile. Particularly preferred are the homopolymers of acrylic acid and its copolymers with one or more of aconitic, fumaric, itaconic, maleic, mesaconic, methacrylic, muconic or tiglic acid, particularly copolymers of acrylic acid and itaconic acid. Especially preferred are those described and claimed in our Complete Specification No. 1,484,454. Good results have also been obtained using a copolymer of vinyl methyl ether and maleic acid.

It is also possible to use a precursor of a poly(carboxylic acid) as (i); as used in this specification, "precursor" means a polymer which will be transformed into the poly(carboxylic acid) on hydrolysis, for example a poly(carboxylic acid anhydride); furthermore, polyacrylic acids may be prepared by hydrolysis of corresponding polyacrylonitriles. The precursor of a poly(-carboxylic acid) may be a homopolymer of an unsaturated carboxylic acid anhydride or a copolymer with an above mentioned other carboxylic acid or anhydride thereof; or a copolymer of an unsaturated carboxylic acid (anhydride) with an unsaturated aliphatic monomer, for example vinyl monomers, such as vinyl hydrocarbon monomers, vinyl ethers, acrylamide or acrylonitrile. Good results may be obtained by using homopolymers of maleic anhydride or vinyl orthophthalic anhydride, or copolymers thereof, especially block copolymers thereof, with ethylene, propylene, butenes, styrene, and vinyl methyl ether.

The poly(carboxylic acid) or precursor thereof is preferably linear, although branched polymers may also be used. Preferably, the polymer has an average molecular weight from 1,000 to 1,000,000, more preferably from 1,000 to 250,000, and most preferably from 5,000 to 100,000, especially from 10,000 to 25,000. In this specification the average molecular weight is defined as being that measured by ultracentrifuging.

The preferred particulate ion-leachable silicates or aluminosilicates (ii) are glasses wherein the ratio by weight of acidic to basic oxides in the glass is such that the glass will react with (i) in the presence of water to set to a hardened composition. The principal acidic oxide in the aluminosilicate glass is a silica, although the glass may also contain minor amounts of other anhydrides such as phosphorus pentoxide and boric oxide. The principal basic oxide in the glass is alumina which, although it has amphoteric properties, can be considered for the purposes of the present invention solely as a basic oxide. Particularly preferred aluminosilicate glasses fall within the composition range of 10 to 65% w/w silica and 15 to 50% w/w alumina.

The aluminosilicate glass desirably contains at least one other basic oxide, preferably calcium oxide, which may be present in the glass composition in an amount from 0 to 50% w/w. The calcium oxide may be partly or wholly replaced by sodium oxide or other basic oxide or a mixture of basic oxides, although in some applications the presence of sodium oxide may be undesirable as this oxide tends to increase the solubility of the resulting cement. Preferred glasses for use in the present invention containing alumina, silica and calcium oxide are the gehlenite and anorthite glasses, and in general glasses falling within the composition range 10 to 65% w/w silica, 15 to 50% w/w alumina and 0 to 50% w/w calcium oxide.

Other aluminosilicate glasses suitable for use in the present invention may contain fluoride, suitably up to 15% by weight preferably less than 10% by weight. A class of fluoroaluminosilicate glasses particularly suited to dental applications are those wherein the ratio by weight of silica to alumina is from 1.5 to 2.0 and the ratio by weight of silica to alumina is from 0.5 to 1.5 and the ratio by weight of fluorine to alumina is from 0.25 to 2.0.

The aluminosilicate glasses suitable for use in the present invention may be prepared by fusing mixtures of the components in the appropriate proportions at temperatures above 900° C. and preferably in the range of 1050° C. The mixture is preferably fused from 1 to 4 hours. Silica and alumina may be included in the mixture as oxides, though it is convenient to add calcium oxide and sodium oxide as calcium carbonate and sodium carbonate respectively, and reference to the presence of these oxides in a glass fusion mixture includes the possibilities that they may be added as carbonates or as other compounds which decompose similarly under glass fusion conditions to give the oxides.

The addition of carbonates to the fusion mixture lowers the fusion temperature and thus these can be considered as fluxing agents. If desired, however, the mixture may contain an additional fluxing agent, and this has been found to be important with glass compositions containing less than 10% w/w of calcium oxide. In this connection, fluorides such as fluorite and cryolite have been found to be especially useful as fluxing agents, although it is desirable not to use large amounts of fluorides in the fusion mixture. Other fluxing agents, for example calcium phosphate and aluminium phosphate may also be used. The total amount of fluxing agents present in the mixture, including carbonates, may be up to 50% by weight, based on the total weight of mixture.

After fusion the glass may be poured off and cooled rapidly, for example, in air or water or some combination of both. To the first approximation the proportions of the same elements are present as in the mixture. Some fluorine may, however, be lost from the fluoride fluxing agent during the reaction.

Glasses used in the present invention may be readily obtained in fine powder form. The degree of fineness of the powder should preferably be such that it produces a smooth cement paste which sets within an acceptable period when mixed with the poly(carboxylic acid) in the presence of water. Preferably the degree of fineness of the powder is such that it will pass through a 150 mesh B.S. sieve and most preferably such that it will pass through a 350 mesh B.S. sieve. Mixtures of different glasses may be used if desired. Preferred are (fluor-)aluminosilicate glass powders.

The silicate may also be a naturally-occurring orthosilicate, pyrosilicate, cyclic or chain silicate comprising recurring metasilicate units, or aluminosilicate having an Al:Si molar ratio greater than 2:3; or blast furnace slags; or Portland cement. Examples of such materials include aphrosiderite, danalite, gehlenite, hemimorphite, larnite, levynite, nepheline, muscovite, solalite, scolecite, spurrite, thuringite, willemite, wollastonite (including calcined wollastonite).

This invention also provides a mixture, which may be aqueous, of a metal salt (iii) as herein defined with a complexing agent as herein defined, or a poly(carboxylic acid) (i) as herein defined, or both. In the absence of water the poly(carboxylic acid) may be present as a precursor, as herein defined.

The hardenable composition of the invention may be supplied or stored in any suitable manner providing that means are provided to prevent reaction of the ion-leachable particulate material (ii) with the poly(carboxylic acid) (i) in the presence of water. Thus, the composition may be supplied or stored as a dry mixture, suitably comprising an intimate powder, of the poly(carboxylic acid) or precursor thereof (i) in particulate form; particulate ion-leachable silicate or aluminosilicate (ii); and metal salt (iii). When the latter is in powder form, it preferably has a degree of fineness such that it will pass through a 150 B.S. mesh sieve.

It is also possible to supply or store the composition as a two-component pack, one of which pack components may comprise an aqueous medium; indeed it may simply comprise distilled water, optionally tinted. In many cases, however, it is found that mixing, and the physical properties of the resulting cement, are improved by providing the poly(carboxylic acid) or metal salt (iii) or complexing agent, all as herein defined, as an aqueous solution which may suitably comprise a mixture as hereinabove defined of such constituents. Such aqueous solutions may contain from 20 to 65% by weight of the poly(carboxylic acid). Where the metal salt (iii) is also inclined in that solution it must be free from any tendency to precipitate the poly(carboxylic acid) (i). It may instead be included in admixture with the particulate ion-leachable silicate or aluminosilicate (ii) or indeed in both. It may be found convenient to include the metal salt (iii) in an aqueous solution while the poly(carboxylic acid) or precursor thereof (i) is in dry admixture with the particulate ion-leachable silicate or aluminosilicate (ii). Furthermore, any chelating agent present may be included either with the particulate ion-leachable silicate or aluminosilicate (ii) or in an aqueous phase.

In addition, hardenable compositions according to the present invention may comprise an amount of filler, suitably from 10 to 65%, preferably 25 to 50%, by weight of filler of the total weight of the components.

Such materials include sand, talc, and fibrous materials such as asbestos and nylon. Inclusion of an inert filler is found to minimise any problem of contraction and cracking of the hardened composition which may occur.

Furthermore, where the hardened composition is intended for use in a low humidity environment it is found beneficial to incorporate, in the hardenable composition, an amount, suitably from 5 to 70% by weight, of an emulsion of a substantially water-insoluble polymer, particularly a polymer comprising carboxyl groups capable of participating in the setting reaction to form the hardened composition. Examples of such water-insoluble polymers include copolymers of unsaturated aliphatic carboxylic acids, such as acrylic acid, methacrylic acid or itaconic acid, with unsaturated aliphatic esters, such as methyl methacrylate, ethyl methacrylate and ethyl acrylate.

The hardenable compositions of this invention may be used as dental cements and have many applications in dentistry including use as filling materials for restoring teeth and for cementing inlays and crowns into place in the tooth; as luting compositions to provide a base and/or lining in a tooth cavity or a temporary fixing for the bonds of orthodontic appliances to the teeth; and as compositions for sealing root canals after endodontic treatment. They may also be formed as hardenable sheet materials, for example by depositing the components, optionally in intimate admixture, upon a flexible support web which may be woven, laid down as a non-woven fabric, cast or extruded. Preferably such a flexible support web may be a cotton bandage fabric, for example of leno weave. Such sheet materials have important surgical applications such as splinting materials. They may also be used in forestry (to repair and support damaged branches) and as modelling materials. The hardenable compositions may also be used in the building industry as surface coatings, flooring materials, speciality cements, including groutings, panellings, shuttering and adhesives. They may also be used to seal exposed and hazardous asbestos surfaces and claddings as disclosed in our copending U.K. Patent Application No. 1834/78. The hardened compositions also provide a binder for foundry sand which has the merit that while used in small amounts it provides good green strength for the bound sand yet, after investment, gives a readily friable, recyclable foundry sand. The hardened compositions are also useful as moulds for ceramic articles.

Stannous fluoride containing compositions are found to be radio-opaque, a property useful in dentistry.

The following Examples illustrate the invention; in these Examples the composition of the fusion mixture of the glasses by weight is as shown in Table 1.

TABLE 1

| | COMPOSITION OF GLASS FUSION MIXTURES | | | | | | | | |
|---|---|---|---|---|---|---|---|---|---|
| Glass | $SiO_2$ | $Al_2O_3$ | $CaCO_3$ | $MgCO_3$ | $Na_3AlF_6$ | $CaF_2$ | $AlF_3$ | $AlPO_4$ | $Ca(PO_4)_2$ |
| 1 | 175 | 100 | | | 30 | 207 | 32 | 60 | |
| 2 | 175 | 100 | | | | | | 60 | 220 |
| 3 | 100 | 100 | | | | | | | 200 |
| 4 | 160 | 100 | | | | | | | 140 |
| 5 | 120 | 102 | 300 | | | | | | |
| 6 | 360 | 102 | 200 | | | | | | |
| 7 | 180 | 102 | 100 | | | | | | |
| 8 | 240 | 68 | 200 | | | | | | |
| 9 | 60 | 102 | 200 | | | | | | |
| 10 | 300 | 102 | | 365 | | | | | |
| 11 | 180 | 102 | | 183 | | | | | |
| 12 | 300 | 102 | | 183 | | | | | |

Percentages are by weight

EXAMPLE 1

This Example illustrates the effect of various salts on the setting time of the slow-setting glass 8.
The results are shown in Table 2.

TABLE 2

| | SETTING TIMES (MIN) | |
|---|---|---|
| | A | B |
| Aluminium fluoride | 145 | 25 |
| Barium chloride | 330 | 60 |
| Barium fluoride | >420 | 23 |
| Bismuth phosphate | >420 | 60 |
| Cadmium sulphate | 240 | 15 |
| Calcium chloride | >420 | >420 |
| Copper chloride | >420 | 270 |
| Magnesium fluoride | 140 | 20 |
| Mercuric chloride | 310 | 53 |
| Stannous chloride | >420 | 6 |
| Stannous fluoride | 128 | 12 |
| Silver difluoride | 22 | 11 |
| Silver nitrate | 17 | 18 |
| Sodium fluoride | >420 | >420 |
| Zinc chloride | >420 | 47 |
| Zinc fluoride | 250 | 15 |
| Zirconium oxychloride | 72 | 10 |
| Metal additive | >420 | >420 |

With no additives the setting time was greater than 420 mins.
A: no tartaric acid in liquid; 10% of metal salt in powder.
B: 5% tartaric acid in liquid; 10% of metal salt in powder.

EXAMPLE 2

This Example illustrates the effect of stannous fluoride on the compressive strength of certain glasses. Curing of the hardened composition was effected at 37° C. for 24 hours in each case.

Cylinders of cement (12 mm long and 6 mm in diameter) were prepared in sealed moulds cured at 37° C. for 1 hour and then placed either into water or liquid paraffin, at 37° C., for a further 23 hours.

The results are shown in Table 3.

TABLE 3

| | CEMENT STRENGTH (N/mm²) | | | | |
|---|---|---|---|---|---|
| Glass | A | B | C | D | E |
| 1 | 165 | | 97 | 153 | 95 |
| 3 | 3.3* | 69* | 16 | 79* | |
| 7 | 31* | | 90* | 33* | 96* |

TABLE 3-continued

| | CEMENT STRENGTH (N/mm$^2$) | | | | |
|---|---|---|---|---|---|
| Glass | A | B | C | D | E |
| 11 | 31* | 51* | | 48* | 69* |

*In these cases curing was effected in liquid paraffin.
A: No additives.
B: No tartaric acid in liquid: 1% SnF$_2$ in powder.
C: No tartaric acid in liquid: 10% SnF$_2$ in powder.
D: 5% tartaric acid in liquid: no SnF$_2$ in powder.
E: 5% tartaric acid in liquid: 10% SnF$_2$ in powder.

EXAMPLE 3

This Example illustrates the effect of stannous fluoride on the working time and setting rate (relative to glass 1) on certain glasses.

Cement pastes were prepared at 23° C. and an oscillating rheometer [1] was employed to determine their working time and setting rate at 23° C. following a set procedure [2].

[1] S. C. Bovis, E. Harrington and H. J. Wilson (1971) Br. dent J, 131, 352.
[2] A. D. Wilson, S. Crisp and A. J. Ferner (1976) J, dent Res, 55, 489.

The results are shown in Table 4.

TABLE 4

| | WORKING TIMES AND SETTING RATES (at 23° C.) | | | | | | | | | |
|---|---|---|---|---|---|---|---|---|---|---|
| | A | | B | | C | | D | | E | |
| Glass | Working time (min.) | relative setting rate | Working time (min.) | relative setting rate | Working time (min.) | relative setting rate | Working time (min.) | relative setting rate | Working time (min.) | relative setting rate |
| 1 | 4.25 | 1 | | | 2.25 | 0.2 | 2.75 | 3.3 | 1.5 | 3.3 |
| 5 | 0.75 | 4 | 0.5 | 4 | | | 1.25 | 3.3 | 0.5 | 6.7 |
| 7 | 2 | 1.1 | | | 1.5 | 3.3 | 2.75 | 2.0 | 0.75 | 5 |
| 10 | 3.25 | 1.1 | | 2 | 3.25 | | 2.25 | 2.6 | 1.5 | 2.5 |
| 11 | 6.5 | 0.9 | 4.25 | 2 | | | 7 | 0.22 | 2.75 | 0.9 |

A: No additives
B: No tartaric acid in liquid; 1% SnF$_2$ in powder
C: No tartaric acid in liquid; 10% SnF$_2$ in powder
D: 5% tartaric acid in liquid; no SnF$_2$ in powder
E: 5% tartaric acid in liquid; 10% SnF$_2$ in powder

EXAMPLE 4

This Example illustrates the effect of stannous fluoride on the relative setting rate of a greater variety of glasses. A ranking order for the effect of additives, is given for each glass.

The results are shown in Table 5.

TABLE 5

| Glass | A | B | C | D |
|---|---|---|---|---|
| 2 | 4 | 2 | 3 | 1 |
| 3 | 4 | 2 | 3 | 1 |
| 4 | 4 | 2 | 3 | 1 |
| 5 | 2 | 1 | 3.5 | 3.5 |
| 7 | 4 | 3 | 2 | 1 |
| 8 | 4 | 3 | 2 | 1 |
| 9 | 4 | 3 | 2 | 1 |
| 10 | 4 | 3 | 2 | 1 |
| 11 | 4 | 3 | 2 | 1 |

4 represents the longest, 1 the shortest, setting time.
A: No additives.
B: No tartaric acid in liquid, SnF$_2$ in powder.
C: 5% tartaric acid in liquid.
D: 5% tartaric acid in liquid, SnF$_2$ in powder.

EXAMPLE 5

This Example illustrates the effect of stannous fluoride on the setting time of glasses and minerals at 37° C.

Setting of cement pastes (at 37° C.) were determined at 37° C. using the method disclosed in International Standards Organisation Recommendation 1SO/R 1565.

The results are shown in Table 6.

TABLE 6

| SETTING TIMES OF VARIOUS CEMENT COMPOSITIONS | | | | | | |
|---|---|---|---|---|---|---|
| Glass or Mineral | SETTING TIME (MIN) at 37° C. | | | | | |
| | A | B | C | D | E | F |
| 1 | 7.5 | | 4.75 | 4 | | 4 |
| 2 | 47 | | 22 | 24 | | 8.25 |
| 3 | >240 | | 74 | 120 | | 29 |
| 4 | 44 | | 8.25 | 13.25 | | 5 |
| 5 | 3 | 2.5 | | 3.25 | 3.25 | |
| 6 | >1860 | | >1860 | >1800 | | 1410 |
| 7 | 34 | | 14.5 | 9 | | 5.25 |
| 8 | >240 | | 128 | 38.25 | | 11.75 |
| 9 | 7.5 | 7 | | 4.25 | 3.75 | |
| 10 | 34.75 | 25.75 | | 8.25 | 6.5 | |
| 11 | 29 | 19.5 | | 10.75 | 7.25 | |
| 12 | | | >3180 | | | |
| Muscovite | 9.75 | | 8.75 | 5.5 | | 5 |
| Chlorite | 50 | | 34.75 | 45 | | 49 |
| Dioptase | 37 | | 13 | 23 | | 76 |
| Scolecite | 9.5 | | 8.75 | 4.5 | | 4.25 |
| Riebeckite | 397 | | >450 | 125 | | >1260 |
| Nontronite | 57.25 | | 38.75 | 24.25 | | 20.75 |

A: No additives
B: No tartaric acid in liquid, 1% SnF$_2$ in powder
C: No tartaric acid in liquid, 10% SnF$_2$ in powder
D: 5% tartaric acid in liquid, No SnF$_2$ in powder
E: 5% tartaric acid in liquid, 1% SnF$_2$ in powder
F: 5% tartaric acid in liquid, 10% SnF$_2$ in powder.

EXAMPLE 6

This Example illustrates the effect of various salts on the hydrolytic stability of a selection of glasses.

Cylinders of cement (12 mm long and 6 mm in diameter) were prepared in sealed moulds and stored at 37° C. for either 1 hour or 24 hours before immersing in water. Hydrolytic stability was ascertained visually and a cement was considered to be hydrolytically unstable if visible signs of disintegration were observed. Strength measurements were made 48 hours after cement preparation.

The results are shown in Tables 7 and 8.

TABLE 7

| EFFECTS ON ADDITIVES ON THE HYDROLYTIC STABILITY AND COMPRESSIVE STRENGTH OF OXIDE GLASSES | | | | | | | | | | | | | |
|---|---|---|---|---|---|---|---|---|---|---|---|---|---|
| Glass | Control | AlF$_3$ | AlF$_3$ + T | MgF$_2$ | MgF$_2$ + T | SnF$_2$ | SnF$_2$ + T | ZnF$_2$ | ZnF$_2$ + T | ZrOCl$_2$ | ZrOCl$_2$ + T | AgNO$_3$ | AgNO$_3$ + T |
| 4 | | | | | | | | | | | | | |
| 10% | | | | | | | | | | | | | |

TABLE 7-continued

EFFECTS ON ADDITIVES ON THE HYDROLYTIC STABILITY AND COMPRESSIVE STRENGTH OF OXIDE GLASSES

| Glass | Control | $AlF_3$ | $AlF_3$ + T | $MgF_2$ | $MgF_2$ + T | $SnF_2$ | $SnF_2$ + T | $ZnF_2$ | $ZnF_2$ + T | $ZrOCl_2$ | $ZrOCl_2$ + T | $AgNO_3$ | $AgNO_3$ + T |
|---|---|---|---|---|---|---|---|---|---|---|---|---|---|
| additive 1 hr. hydrolytic stability | S | S | S | S | S | S | S | S | S | S | S | S | S |
| 24 hr. hydrolytic stability | S | S | S | S | S | S | S | S | S | S | S | S | S |
| 2 day CS $N/mm^2$ | 72 | 91 | 112 | 101 | 158 | | 144.6 | 111 | 128 | 55 | 83 | 47 | 66 |
| 8 10% additive 1 hr. hydrolytic stability | U | | | | | U | | U | | U | | | |
| 24 hr. hydrolytic stability | U | U | S | U | U | U | S | U | S | U | U | U | S |
| 2 day CS $N/mm^2$ | | | 2.6 | | | | 40 | | 6 | | | | 2.6 |
| 11 1% additive 1 hr. hydrolytic stability | U | | S | | S | | S | | | | S | | S |
| 24 hr. hydrolytic stability | U | | | S | S | U | S | | | | | S | S |
| 2 day CS $N/mm^2$ | | 7.5 | 30 | 8.4 | 31 | | 43 | 15.75 | 43.6 | 6.2 | 24.5 | 6.6 | 27.5 |

S - Stable
U - Unstable
T - Tartaric acid added to liquid

TABLE 8

THE EFFECT OF ADDITIVES ON THE HYDROLYTIC STABILITY AND COMPRESSIVE STRENGTH OF OXIDE GLASSES REPRESENTED IN RANKING ORDER

| Glass | $AlF_3$ | $AlF_3$ + T | $MgF_2$ | $MgF_2$ + T | $SnF_2$ | $SnF_2$ + T | $ZnF_2$ | $ZnF_2$ + T | $ZrOCl_2$ | $ZrOCl_1$ + T | $AgNO_3$ | $AgNO_3$ + T |
|---|---|---|---|---|---|---|---|---|---|---|---|---|
| 4 | | 2 | | 5 | | 4 | | 3 | | 1 | — | — |
| 8 | 0 | 1 | 0 | 0 | 0 | 3 | | 2 | 0 | 0 | 0 | 1 |
| 11 | 2 | 3 | 3 | 4 | 0 | 5 | 4 | 5 | 1 | 1 | 1 | 2 |

— indicates a decrease in control properties
0 represents no improvement in control properties
Lowest number represents the least improvement in control properties
highest number the greater improvement.

We claim:

1. A hardenable composition which comprises (i) a poly(carboxylic acid) selected from the group consisting of homopolymers and copolymers of unsaturated aliphatic carboxylic acids or precursor thereof that is converted to said poly(carboxylic acid) on hydrolysis thereof; (ii) a particulate ion-leachable silicate or aluminosilicate glass reactable with (i) in the presence of water to set to a hardened composition; and (iii) an inorganic metal salt which accelerates the setting of the composition selected from the group consisting of a silver (I) salt, a barium salt and a multivalent metal salt, the cation of which has a standard electrode potential $E_{ox}^o$ less than 2.6 volts.

2. A hardenable composition according to claim 1 wherein (iii) comprises a silver (I) salt or a barium salt.

3. A hardenable composition according to claim 2 wherein (iii) comprises silver nitrate, barium chloride or barium fluoride.

4. A hardenable composition according to claim 1 wherein (i) comprises an acrylic acid homopolymer or copolymer of acrylic acid with one or more of aconitic, fumaric, itaconic, maleic, mesaconic, methacrylic, muconic, or tiglic acid.

5. A hardenable composition according to claim 1 wherein (iii) comprises a multivalent metal salt the cation of which has a standard electrode potential $E_{ox}^o$ less than 2.6 volts.

6. A hardenable composition according to claim 5 wherein (iii) comprises a salt of aluminium, cadmium, magnesium, mercury (II), silver (II), or zirconium.

7. A hardenable composition according to claim 6 wherein (iii) comprises a salt of aluminium, magnesium, silver (II) or zirconium.

8. A hardenable composition according to claim 1 wherein (iii) comprises a fluoride.

9. A hardenable composition according to claim 8 wherein (iii) comprises aluminium fluoride, magnesium fluoride, stannous fluoride, silver difluoride or zinc fluoride.

10. A hardenable composition according to claim 1 wherein (iii) is soluble in an aqueous solution of (i).

11. A hardenable composition according to claim 1 which further comprises a complexing agent soluble in an aqueous solution of (i).

12. A hardenable composition according to claim 11 wherein the complexing agent comprises a fluoride ligand.

13. A hardenable composition according to claim 11, wherein the complexing agent comprises a chelating agent.

14. A hardenable composition according to claim 13 wherein the chelating agent comprises a plurality of carboxyl groups.

15. A hardenable composition according to claim 14 wherein the chelating agent comprises aconitic, itaconic, maleic, mellitic or tricarballic acid.

16. A hardenable composition according to claim 13 wherein the chelating agent also comprises at least one hydroxyl group.

17. A hardenable composition according to claim 16 wherein the chelating agent comprises citric, malic or tartaric acid.

18. A hardenable composition according to claim 13 wherein the chelating agent comprises a multivalent metal chelate.

19. A hardenable composition according to claim 18 wherein the chelating agent comprises a beta-diketone metal chelate or an EDTA chelate.

20. A hardenable composition according to claim 18 wherein the multivalent metal is the same as that in (iii).

21. A hardenable composition according to claim 13 wherein (iii) comprises a multivalent metal fluoride or a multivalent metal chloride the cation of which has a standard electrode potential $E_{ox}^o$ less than 2.6 volts.

22. A hardenable composition according to claim 1 wherein (iii) is present in an amount of up to 15% by weight, based on the weight of (i).

23. A hardenable composition according to claim 13 wherein the weight ratio of (iii) to the chelating agent is from 15:1 to 1:15.

24. A hardenable composition according to claim 1 wherein (ii) comprises a (fluor)aluminosilicate glass powder.

25. A hardenable composition according to claim 1 comprising a dry mixture of the poly(carboxylic acid) or precursor thereof (i) in particulate form; particulate ion-leachable silicate or aluminosilicate (ii); and metal salt (iii).

26. A hardenable composition according to claim 1 supplied as a two-component pack, one of which components may comprise an aqueous medium.

27. A hardenable composition according to claim 1 supplied as a sheet material.

* * * * *